United States Patent [19]

Goedemans

[11] Patent Number: 4,705,678
[45] Date of Patent: Nov. 10, 1987

[54] STERILE RADIOACTIVE INDIUM-CONTAINING AQUEOUS SOLUTION

[75] Inventor: Wilhelmus T. Goedemans, Schoorldam, Netherlands

[73] Assignee: Mallinckrodt, Inc., St. Louis, Mo.

[21] Appl. No.: 626,080

[22] Filed: Jun. 29, 1984

[30] Foreign Application Priority Data

Jul. 7, 1983 [NL] Netherlands ............... 8302422
Dec. 2, 1983 [NL] Netherlands ............... 8304142

[51] Int. Cl.$^4$ .................................. A61K 49/00
[52] U.S. Cl. ........................... 424/1.1; 424/9
[58] Field of Search ..................... 424/1.1, 9

[56] References Cited

U.S. PATENT DOCUMENTS

| | | | |
|---|---|---|---|
| 3,991,173 | 11/1976 | Sinn et al. | 424/1.1 |
| 4,335,095 | 6/1982 | Kelly | 424/9 |
| 4,348,375 | 9/1982 | Goedemans | 424/1.1 |
| 4,360,509 | 11/1982 | Goedemans | 424/9 |
| 4,443,426 | 4/1984 | Thakur | 424/1.1 |
| 4,497,791 | 2/1985 | Gamble et al. | 424/9 |

OTHER PUBLICATIONS

Dewanjee et al., J. Nuclear Med. 22(11) 1981,981-7.
Peters et al., J. Nucl. Med. 24(1983) 39-44.

*Primary Examiner*—Christine M. Nucker
*Attorney, Agent, or Firm*—R. J. Klostermann; L. N. Goodwin

[57] ABSTRACT

The invention relates to a sterile aqueous solution for radioassaying a radioactive indium compound, which solution is entirely or substantially free from organic solvent, has a pH from 4 to 9, comprises a radioactive indium tropolonate or pyrithionate and has been subjected to a thermal sterilization.

The invention also relates to the radioactive labelling of blood cells by treating a suspension of the blood cells with a sterile solution of a radioactive indium compound, in which either (a) a carbon-dioxide-generating substance is previously incorporated in the solution, or (b) a substance which under the labelling conditions generates carbon dioxide is added to the cell suspension, or carbon dioxide is passed through the cell suspension prior to or during the treatment.

The invention furthermore relates to a kit for the radioactive labelling of blood cells.

8 Claims, No Drawings

STERILE RADIOACTIVE INDIUM-CONTAINING AQUEOUS SOLUTION

The invention relates to a sterile aqueous solution comprising a radioactive indium compound for radioassaying which is entirely or substantially free from organic solvent and which has a pH from 4 to 9. The invention further relates to a method for the radioactive labelling of blood cells and to a kit suitable therefor, as well as to a method for radioassay.

A sterile aqueous solution for radiologic examination comprising a sterile radioactive indium compound as mentioned in the opening paragraph is known from literature. European patent application No. 17355 discloses a solution of indium-111 oxinate suitable for labelling blood cells. It appears from the experiments described in the said patent application that up to approximately 40% of the radioactivity may be retained in the vial after autoclaving the aqueous indium oxinate solution. The attachment (adhesion) of the radioactive complex to the glass surface of the reservoir is considerably reduced by the addition of a surface-active substance, for example, a fatty acid polyoxyethylene sorbitan ester. Autoclaving is to be understood to mean herein the sterilization of the solution under the influence of heat in an autoclave. It has been found that the same problems occur when plastics reservoirs are used. Thakur c.s. suggested in J. Nucl. Med. 18, 1012–1019 (1977) to add ethanol to improve the solubility of indium-111 in water at approximately neutral pH.

The additives which improve solubility, for example, surface-active substances, or ethanol, however, may be potentially toxic with respect to the blood cells to be labelled and can hence adversely influence the viability of the cells. It is intended to inject the blood cells after labelling into a warm-blooded being, in particular a human being, and to subject him subsequently to a radioassay. A technique of external imaging is used to detect accumulated radioactivity and to thus determine its location in the body. In this way, dependent on the kind of the labelled blood cells, e.g. thrombi, arterial damage, or body inflammations or abcesses can be localized.

It will be obvious that for this purpose only labelled blood cells are useful which still have sufficient viability to accumulate through the blood circulation system in, for example, the inflamed area of the body. Therefore, any adverse influence of the viability of the blood cells during labelling should be avoided.

U.S. Pat. Specification No. 4,348,375 relates to an aqueous, radioassaying solution of indium oxinate which is entirely or substantially entirely free from organic solvent. In order to reduce the adsorption of indium-111 to the glass equipment with which the radioactive material contacts, it is recommended to carry out the autoclaving at a pH below 4.2. Prior to use, the pH of the labelled cell suspension should be brought at approximately 6 to 7. However, such a neutralization with a sterile buffer solution under aseptic conditions involves a considerable burden for the user. Moreover, this extra process should be carried out in a room in a clinic or laboratory suitable for working with radioactive isotopes.

It has now been found that the above-mentioned problems can be avoided by having the solution for radiologic examination mentioned in the opening paragraph to comprise a radioactive indium tropolonate or pyrithionate. Another name for pyrithion is 2-mercaptopyridine-1-oxide. It has been found that this solution can be sterilized at neutral pH by means of heat without any problem. Indium tropolonate is to be preferred because it has been accepted in practice on the basis of its physiological properties.

An aqueous solution of indium tropolonate is known from literature, for example from an article by Danpure c.s. in Brit. J. Radiol. 55, 247–249 (1982). However, neither in this article, nor in other publications on this subject is a heat-sterilized or autoclaved indium tropolonate solution described. Nevertheless it is desirable, and in many cases even prescribed by the authorities, to use, for the treatment of blood cells to be introduced again into the body, an agent which is acceptable from a pharmaceutical point of view, consequently which is heat-sterilized. In view of the problems which occur upon autoclaving an aqueous indium-111 oxinate solution, it was expected that the same detrimental phenomena would occur upon using indium tropolonate or pyrithionate upon autoclaving the solution. It has surprisingly been found, however, that an aqueous solution of radioactive indium tropolonate or pyrithionate shows hardly any adhesion to the glass wall during heat-sterilization. In this respect an aqueous solution of the said indium compounds is to be preferred over a radioactive indium oxinate solution.

Of the radioactive indium isotopes, indium-111 is best suitable for the above-mentioned radiologic determinations, for example the localization of body inflammations, because it has a half-life of approximately 67 hours. Moreover, indium-111 can in a simple manner be produced in a cyclotron and is amply available. So the invention relates in particular to an aqueous solution as described hereinbefore, in which indium-111 tropolonate or pyrithionate is dissolved as the radioactive indium compound. The heat sterilization is carried out under heat sterilizing conditions, preferably by heating the solution at approximately 120° C. in an autoclave for approximately 20 minutes.

A solution suitable for radiologic examination, for example, for labelling blood-cells, preferably comprises indium-111 tropolonate or pyrithionate in a quantity sufficient to label the blood-cells, e.g., of approximately 0.0005 to 0.2 mg per ml. It is advantageous that the solution comprises in addition sufficient sodium chloride so that the solution is isotonic. In that case the solution will preferably comprise approximately 0.1 to 1 g of sodium chloride per 100 g of solution.

The solution according to the invention has a pH between 4 and 9, preferably an approximately physiological pH. For that purpose the solution usually comprises one or more buffers in a buffering amount, for example, TRIS [tris(hydroxymethyl)aminomethane] or HEPES [N-2-hydroxy- ethylpiperazine-N'-2-ethane sulphonic acid]. In addition to sodium chloride the solution may comprise other salts such as sodium acetate and/or sodium phosphate. A sterile solution of a radioactive indium compound according to the invention may be prepared by dissolving the desired quantity of the radioactive indium tropolonate or pyrithionate in water or saline and then thermally sterilizing the resulting solution, preferably in an autoclave.

The solutions according to the present invention may be used for radioassaying, for example, for labelling blood-cells in vitro or in vivo. The blood-cells to be labelled may be red or white cells or blood platelets. When labelling in vitro, the blood-cells to be labelled are generally isolated from a blood sample and then, after suspending in, for example, blood plasma or physiological saline, labelled and introduced into the body of a warm-blooded living being, in particular a human being. In the in vivo method the solution to be used for labelling is administered directly into the body, labelling taking place in situ. Labelling then may be less selective with regard to the various blood-cells present. In both methods the location where the radioactivity accumulates in the body can be determined by external imaging. When, for example, the in vivo method is used for localizing an abscess or another inflammation process in the body, the sterile aqueous solution of the radioacive indium tropolonate or pyrithionate is introduced into the bloodstream of the living being. After a given period, the radioactive indium compound has accumulated, not only in certain areas of the body, such as the liver and the spleen, but also in comparatively large quantities in the inflamed area in question. The body may then be subjected to a radio assay by an external imaging technique to detect the accumulated radioactivity in the location of the inflamed area, provided said area is in another part of the body than in which the radioactivity would accumulate to substantially the same extent even in the absence of an inflamed area.

In the in vitro labelling method, the solution according to the invention comprising radioactive indium may be used to label cellular blood components, for example, granulocytes, lymphocytes, blood platelets, and erythrocytes. These labelled cells may be used, for example, to localize body organs, abscesses and other inflammatory processes, myocardiac infarcts, thrombus formulations and rejection of transplanted organs, as described hereinbefore for the in vivo method. Labelled erythrocytes may also be used to measure the blood volume. Indium-111 labelled erythrocytes, 24 hours after intravenous administration, show activity in the blood pools of heart, liver and spleen. The solution according to the invention may further be used for many other purposes.

The labelling of blood-cells may be carried out by adding the radioactive indium-containing solution to a cell preparation which is preferably suspended in buffered saline, blood plasma or in another suitable physiological medium. After gently mixing, the mixture may at least twenty minutes be incubated at room temperature to obtain efficient labelling. The labelling efficiency depends on the number of cells in the incubation mixture. When the labelling efficiency is insufficient, washing of the cells is recommended to remove all free radioactive indium tropolonate or pyrithionate. Thereafter, the labelled cells may, for example, be resuspended in their own plasma medium. In case of labelling leucocytes and thrombocytes, care should be taken that the isolation procedure for the cells is as minimal as possible to avoid damage to the cells. For example, when isolating human leucocytes it is sufficient to sediment the erythrocytes by gravity at room temperature for one hour. The supernatant plasma to be separated contains nearly all the leucocytes which, preferably after washing once with buffered saline, can be labelled with radioactive indium.

It will be obvious from the above that upon labelling blood-cells the labelling efficiency is of prime importance. Said labelling efficiency, in practice, dependent on the number and kind of the cells in the suspension to be labelled and on the incubation time, usually proves to be not higher than approximately 15 to 25% if the cells are suspended in plasma. The presence of plasma in the suspension to be labelled promotes the maintenance of the viability of said cells. However, plasma has a detrimental effect on the labelling efficiency. It was surprisingly found now that upon labelling blood-cells, in particular when plasma is present, the labelling efficiency can be considerably improved by adding to the cell suspension to be labelled a substance which under the labelling conditions generates carbon dioxide, or by passing carbon dioxide through the cell suspension prior to or during labelling.

The same improvement of the labelling efficiency can be reached by incorporating, also according to the invention, a carbon dioxide-generating substance in the solution comprising the radioactive indium compound to be used for labelling. The latter is to be preferred because it is not necessary for the user of the solution destined for labelling to perform an extra treatment. The invention therefore also relates to a sterile aqueous solution comprising a radioactive indium compound, which solution moreover comprises a carbon dioxide-generating substance, and to the use of the said solution for the radioactive labelling of blood cells.

Although the improvement of the labelling efficiency is most spectacular upon labelling with a solution of a radioactive indium tropolonate, for example, indium-111 tropolonate, the yield of labelled blood-cells can also be increased considerably upon labelling with other radioactive indium compounds, for example, indium-111 pyrithionate, oxinate and acetyl acetonate. It is striking that the strongest increase of the labelling yield is observed upon labelling a suspension of blood-cells in blood plasma. When the blood-cells are suspended in physiological saline or in another medium, in which however, plasma residues will be present, the yield, although to a smaller extent, is nevertheless still significantly improved when carbon dioxide or a carbon dioxide-generating substance is used. Labelling blood-cells which are suspended in blood plasma is of advantage because the cells remain better viable in plasma than in another medium, for example, physiological saline. Therefore, the invented improvement of labelling efficiency, which is considerable, especially in plasma-suspended blood-cells, is of extreme importance. Suitable carbon dioxide-generating substances are bicarbonates, for example, sodium bicarbonate, potassium bicarbonate or ammonium bicarbonate, and lower dialkyl esters of pyrocarboxylic acid, for example, diethyl pyrocarbonate. As will become apparent from the Examples, the labelling efficiency upon labelling an erythrocyte suspension in blood plasma with an aqueous solution of indium-111 tropolonate could be increased by a factor of 3 both when using a carbon dioxide-generating substance and when flushing with carbon dioxide.

The invention also relates to a method of subjecting a warm-blooded living being, in particular a human being, to a radioassaying. In this examination, a sterile solution of a radioactive indium compound according to the invention or blood cells labelled according to the invention with radioactive indium is administered intravenously or subcutaneously to the being. The quantity of the administered imaging active substance may be quite small but must, of course, be sufficient to enable detection by external imaging. A quantity of approximately 0.1 to 10 millicuries of radioactive material, preferably 0.5 to 3 millicuries, per 70 kg of body weight has proved to be sufficient for this purpose.

After the radioactive imaging active substance has been introduced into the body of the living being, the radioassay may be accomplished by using a suitable imaging technique. For this purpose a detector suitable for gamma rays, for example, a gamma camera, is used. In general, one hour is enough for sufficient accumulation of the radioactivity in, for example, the inflamed area, so that already approximately one hour after the injection of the radioactive material an image can be obtained of, for example, the inflamed area. However, the life of the radioactive indium-containing imaging active substance is sufficiently extended to enable repetition of the scanning up to several days after injection. On the other hand said life is not so extended that the substance poses an excessive radiation burden to the body. As already stated hereinbefore, the accumulated radioactivity can be detected in various areas of the body, for example in an organ, such as the liver, the spleen or the kidneys, or for example in an inflamed area.

The invention further relates to a so-called "kit", for labelling blood cells with a radioactive indium compound. The kit comprises a sterile solution of a radioactive indium tropolonate or pyrithionate according to the invention and if desired instructions for use with a prescription for labelling a cell suspension with the solution. In another embodiment the kit comprises a sterile solution of a radioactive indium compound and instructions for use stipulating that a substance which generates carbon dioxide under the labelling conditions is added to the suspension of blood-cells to be treated or labelled with the radioactive indium compound, or that prior to or during the treatment of the cell suspension with the solution, carbon dioxide is passed through the cell suspension.

In again another, particularly interesting, embodiment the kit comprises a sterile solution of a radioactive indium compound, in which solution moreover a carbon dioxide-generating substance has been incorporated, and, if desired, instructions for use with a prescription for labelling a cell suspension with the solution. In the last-mentioned embodiment the radioactive indium compound is preferably indium-111 tropolonate and the carbon dioxide-generating substance is sodium bicarbonate, potassium bicarbonate or ammonium bicarbonate.

The invention will now be described in greater detail with reference to the following specific examples.

EXAMPLE I

Adhesion to the glass wall.

Three bottles containing aqueous solutions of indium-111 oxinate, brought to a pH of 7 with TRIS-buffer, were sterilized by heating in an autoclave at 121° C. for 20 minutes.

After pouring out the solutions and rinsing the bottles with physiological saline, the bottles proved to contain 11.4, 9.6 and 7.1%, respectively, of the overall quantity of radioactivity; so, the attachment to the glass was 9.4% on an average.

In an experiment under exactly the same conditions but this time with indium-111 tropolonate instead of indium-111 oxinate, the attachment of the radioactive material to the glass of the bottles was 1.1, 1.0 and 0.9%, so on an average only 1.0% of the overall quantity of radioactivity.

When indium-111 pyrithionate was used, a significantly reduced adhesion of the radioactive material to the glass wall was also found as compared with indium oxinate, namely 3.7%.

EXAMPLE II

Labelling efficiency of a leucocyte suspension.

Human leucocytes, suspended in saline (leucocyte concentration approximately $10^7$ cells per ml) with a small plasma residue, were labelled by adding a solution of indium-111 tropolonate in saline and gently mixing with the suspension; the mixture was then incubated at room temperature for 20 minutes. The labelling efficiency was determined by subsequently centrifuging the mixture in a tube and determining the radioactivity of the tube with respect to the sediment. The labelling efficiency was 24%. When adding 0.068 molar diethyl pyrocarbonate to the cell suspension, a labelling efficiency of 62% was reached. When the experiment was carried out with indium-111 pyrithionate the labelling efficiency increased from 66 to 81%.

EXAMPLE III

Labelling efficiency of an erythrocyte suspension.

Erythrocytes suspended in 33% human serum (erythrocyte concentration approximately $5 \times 10^8$ cells per ml) were labelled with indium-111 oxinate as described in Example II. The oxinate concentration in the incubation mixture was 0.8 ug/ml. Without any addition a labelling efficiency of 25% was found. When adding 0.057 molar diethyl pyrocarbonate the labelling efficiency increased to 35% and when adding 0.226 molar pyrocarbonate it increased to an even 47%. A comparable improvement of the labelling efficiency was found with an incubation time of 1 hour instead of 20 minutes.

When the same labelling was carried out with indium-111 tropolonate instead of indium-111 oxinate, a labelling efficiency was found of 15% without any addition (incubation time 20 minutes). Addition of 0.023 molar diethyl pyrocarbonate caused the labelling efficiency to increase to 40%, addition of 0.113 molar pyrocarbonate event to 60%. When the same labelling was carried out with indium-111 pyrithionate without any addition, a labelling efficiency of 37% was found. Addition of 0.023 molar diethyl pyrocarbonate caused the labelling efficiency to increase to 66% and addition of 0.226 molar diethyl pyrocarbonate to 87%.

EXAMPLE IV

Labelling efficiency of an erythrocyte suspension.

Erythrocytes suspended in 35% human serum were labelled with indium-111 tropolonate as described in Example II. The tropolonate concentration in the incubation mixture was 0.8 ug/ml. The experiment was carried out in duplicate. The labelling efficiency found was 15 and 18%. When prior to the incubation carbon dioxide was passed through the mixture, the labelling efficiency increased in both experiments to approximately 63%.

EXAMPLE V

Labelling efficiency of an erythrocyte suspension.

Erythrocytes suspended in 33% human serum were labelled with indium-111 pyrithionate as described in Example II. The pyrithionate concentration in the incubation mixture was 1.6 ug/ml. The labelling efficiency found was 38%. In the presence of 0.023 molar diethyl pyrocarbonate said labelling efficiency increased to 66%, with 0.057 molar to 78%, with 0.113 molar to 79%, and with 0.226 molar diethyl pyrocarbonate to 87% labelling efficiency.

EXAMPLE VI

Preparation of indium-111 tropolonate in an aqueous sodium bicarbonate solution.

The following solutions were prepared:

A solution of indium-111 chloride in 0.1 N hydrochloric acid with an activity of 4.5–5.5 mCi/ml;

A 1.5% sodium chloride solution, by dissolving 1.5 g of sodium chloride in 100 ml of water;

A 0.1 molar sodium bicarbonate solution by dissolving 0.84 g of sodium bicarbonate in 100 ml of water; and A tropolone solution by dissolving 56 mg of tropolone in 50 ml of 0.1 N hydrochloric acid.

0.1 ml of the above tropolone solution and 2.3 ml of the above sodium chloride solution were added to 1 ml of the above solution of indium-111 chloride. While stirring, 1.1 ml of the above sodium bicarbonate solution were then added dropwise. After sterilizing (autoclaving) the composition was ready for cell labelling.

EXAMPLE VII

Labelling efficiency of a leucocyte suspension.

Leucocytes suspended in 36% plasma were labelled in saline (leucocyte concentration approximately $10^7$ cells per ml) by adding the composition obtained in Example VI and mixing carefully with the suspension. The mixture was then incubated at room temperature for 20 minutes.

The labelling efficiency was determined by then centrifuging the mixture in a tube and determining the radioactivity of the tube with respect to the sediment. The labelling efficiency was 52%.

For comparison, the same leucocyte suspension was labelled with indium-111 oxinate solution in TRIS-acetate buffer. In this case the labelling efficiency was only 30%.

What is claimed:

1. A solution for radioassaying comprising a heat sterile solution of radioactive indium-111 tropolonate, said solution having a pH of from 4 to 9 and being substantially free from organic solvent, said solution additionally containing a substance which under labelling conditions generates carbon dioxide.

2. A solution according to claim 1 wherein the substance is sodium bicarbonate, potassium carbonate or ammonium bicarbonate.

3. A method of radioactively labelling of blood cells comprising mixing a suspension of blood cells with the sterile aqueous solution of claim 1 in the presence of carbon dioxide.

4. A method radioactively labelling of blood cells comprising mixing a suspension of blood cells with the sterile aqueous solution of claim 2.

5. A method of radioactive labelling of blood cells comprising mixing a suspension of blood cells with a heat sterile aqueous solution of radioactive indium-111 tropolonate, said solution having a pH of from 4 to 9 and being substantially free from organic solvent, wherein prior to or during mixing carbon dioxide is passed through the cell suspension.

6. A method of subjecting a warm-blooded living being to a radioassay, comprising administering to the being blood cells which are labeled according to the method of any one of claims 3, 4, or 5 the quantity of administered radioactivity being sufficient for detection by external imaging, and thereafter the being is subjected to external imaging to detect accumulated radioactivity and to thus determine its location in the body of the being.

7. A method according to claim 6 wherein the radioactive material is administered to the living being in a quantity of approximately 0.1 to 10 millicures per 70 kg of body weight.

8. A method according to claim 7 wherein the quantity of radioactive material administered is approximately from about 0.5 to 3 millicures per 70 kg of body weight.

* * * * *